(12) United States Patent
Tarpeh et al.

(10) Patent No.: US 12,596,114 B2
(45) Date of Patent: Apr. 7, 2026

(54) ELECTROCHEMICAL PRE-CONCENTRATION FOR IMPROVED DETECTION OF GASEOUS SPECIES IN WATER

(71) Applicant: The Board of Trustees of the Leland Stanford Junior University, Stanford, CA (US)

(72) Inventors: William A. Tarpeh, Fremont, CA (US); Debbie G. Senesky, Oakland, CA (US); Anand Vikas Lalwani, Stanford, CA (US); Maximillian Holliday, Santa Fe, NM (US); Linchao Mu, Stanford, CA (US); Brandon D. Clark, Stanford, CA (US); Matthew Junjie Liu, Stanford, CA (US); Hang Dong, Palo Alto, CA (US); Jinyu Guo, Stanford, CA (US)

(73) Assignee: The Board of Trustees of the Leland Stanford Junior University, Stanford, CA (US)

( * ) Notice: Subject to any disclaimer, the term of this patent is extended or adjusted under 35 U.S.C. 154(b) by 993 days.

(21) Appl. No.: 17/642,902

(22) PCT Filed: Sep. 18, 2020

(86) PCT No.: PCT/US2020/051554
§ 371 (c)(1),
(2) Date: Mar. 14, 2022

(87) PCT Pub. No.: WO2021/055792
PCT Pub. Date: Mar. 25, 2021

(65) Prior Publication Data
US 2022/0365059 A1 Nov. 17, 2022

Related U.S. Application Data

(60) Provisional application No. 62/903,286, filed on Sep. 20, 2019.

(51) Int. Cl.
*G01N 33/18* (2006.01)

(52) U.S. Cl.
CPC ..... *G01N 33/1893* (2013.01); *G01N 33/1866* (2013.01)

(58) Field of Classification Search
CPC .......... G01N 33/1893; G01N 33/1866; G01N 27/06; G01N 27/22; G01N 33/18
See application file for complete search history.

(56) References Cited

U.S. PATENT DOCUMENTS

| | | | |
|---|---|---|---|
| 4,941,958 A | 7/1990 | Byers | |
| 5,132,094 A | 7/1992 | Godec | |

(Continued)

FOREIGN PATENT DOCUMENTS

| | | |
|---|---|---|
| CN | 101281154 | 10/2008 |
| CN | 101765766 | 6/2010 |

(Continued)

OTHER PUBLICATIONS

Li et al., "Gas sensors based on membrane diffusion for environmental monitoring", 2017, Sensors and Actuators B 243 566-578.

(Continued)

*Primary Examiner* — Jennifer Wecker
*Assistant Examiner* — Steven Ray Castaneda
(74) *Attorney, Agent, or Firm* — LUMEN PATENT FIRM

(57) ABSTRACT

A sensor for gas species in water includes two membranes separating first, second and third chambers. The first and second chambers are separated by an ion exchange membrane, and the second and third chambers are separated by a gas permeable membrane. Water electrolysis in the first and second chambers provides analyte-ions corresponding to an analyte being detected that pass through the ion exchange membrane from the first chamber to the second chamber. Within the second chamber, these analyte-ions (Continued)

generate analyte via the electrolysis. Analyte in the second chamber passes through the gas permeable membrane to arrive at the third chamber. Within the third chamber, the analyte-ion is generated chemically from the analyte. Electrical detection of the analyte-ion in the third chamber provides sensing of the analyte present in the first chamber.

11 Claims, 6 Drawing Sheets

(56) References Cited

U.S. PATENT DOCUMENTS

| | | | |
|---|---|---|---|
| 5,425,869 | A | 6/1995 | Noding |
| 7,592,184 | B2 | 9/2009 | Khalil |
| 2006/0073077 | A1* | 4/2006 | Centanni ............ G01N 33/0032 |
| | | | 436/155 |

| | | | |
|---|---|---|---|
| 2011/0079523 | A1 | 4/2011 | Offenbacher |
| 2018/0284099 | A1 | 10/2018 | Ayyub |
| 2020/0124554 | A1* | 4/2020 | Zhao ...................... G01N 27/06 |
| 2021/0276893 | A1* | 9/2021 | Maurer ................. B01D 61/50 |

FOREIGN PATENT DOCUMENTS

| | | |
|---|---|---|
| CN | 104089994 | 10/2014 |
| CN | 109540218 | 3/2019 |

OTHER PUBLICATIONS

Kuntke et al., "Energy-Efficient Ammonia Recovery in an Up-Scaled Hydrogen Gas Recycling Electrochemical System", 2018, ACS Sustainable Chem. Eng. 6, 7638-7644.

Tarpeh et al., "Electrochemical Stripping to Recover Nitrogen from Source-Separated Urine", 2018, Environ. Sci. Technol. 52, 1453!1460.

* cited by examiner

ELECTROCHEMICAL PRE-CONCENTRATION FOR IMPROVED DETECTION OF GASEOUS SPECIES IN WATER

FIELD OF THE INVENTION

This invention relates to detection of gaseous species in water.

BACKGROUND

There exists a growing problem of water sources being contaminated through agricultural run-off and algal blooms. Recently, a large toxic algae bloom in the Mississippi river caused over 21 beaches to be shut and large financial losses to the fishing industry. Algal blooms are most often a result of excess ammonia and nitrates in the water due to agricultural run-off. What is needed is a cheaper, less power-hungry deployable sensor to measure ammonia levels in water bodies. Current solutions require personnel to physically go and monitor water quality at various points and for continuous and large area monitoring over extensive time periods, this solution is not viable. A long-standing issue with water monitoring and assessment is the indiscriminate output and fouling of sensors that commonly use polymer-derived or paper-based sensing materials. In addition, optical methods that use fluorescence of analytes require high responsivity photodetectors and complex microfluidics along with constant human-in-the-loop necessity. There is a strong need for energy-efficient and long-lasting water sensors that can be deployed over large areas for ammonia monitoring.

SUMMARY

An exemplary embodiment of the invention is a sensor for detection of a gaseous analyte in water, the sensor including:
- i) a first chamber, a second chamber and a third chamber (e.g., 104, 106, 108 respectively on FIGS. 1A-B);
- ii) an ion exchange membrane (e.g., 110 on FIGS. 1A-B) disposed such that ions can pass through the ion exchange membrane between the first chamber and the second chamber;
- iii) a gas permeable membrane (e.g., 112 on FIGS. 1A-B) disposed such that dissolved gas can pass through the gas permeable membrane between the second chamber and the third chamber; and
- iv) an electrical source (e.g., 116 on FIGS. 1A-B) configured to provide a voltage between a first electrode (e.g., 118 on FIGS. 1A-B) in the first chamber and a second electrode (e.g., 120 on FIGS. 1A-B) in the second chamber such that
  - iv-1) an analyte-ion corresponding to the gaseous analyte is generated in the first chamber, and
  - iv-2) the gaseous analyte is generated in the second chamber from analyte-ions that have passed through the ion exchange membrane.

The third chamber includes a solution (e.g., 122 on FIG. 1A) configured to generate the analyte-ion from gaseous analyte that has passed through the gas permeable membrane. Finally, the sensor includes an electrical sensor (e.g., 114 on FIGS. 1A-B) configured to detect a third concentration of the analyte-ion in the third chamber.

Preferably the capture rate (i.e., the fraction of analyte in the first chamber that becomes corresponding analyte-ion in the third chamber) is 90% or more. In such cases, the concentration of the analyte in the first chamber can be determined from the concentration of the analyte-ion in the third chamber either by assuming an ideal capture rate (e.g., 100%) or by calibration according to the actual capture rate. A linear relationship can be established between a first concentration of the analyte-ion in the first chamber and the third concentration of the analyte-ion in the third chamber based on one or more operating parameters of the sensor. These operating parameters can be: applied bias, fluid flow rates, and sensing time.

The example described in detail below has ammonia as the gaseous analyte. However, principles of this work are applicable to any gaseous analyte that can be electrochemically concentrated. Further analytes of interest include, but are not limited to: hydrogen sulfide and carbon dioxide.

The ion exchange membrane can be an anion exchange membrane or the ion exchange membrane can be a cation exchange membrane.

The electrical sensor can be a capacitive sensor. The electrical sensor can be a conductivity sensor. The electrical sensor can be immersed in the third chamber (e.g., 114' on FIG. 1C) or it can be disposed such that it is not immersed in the third chamber (e.g., 114 on FIGS. 1A-B).

Further variations are possible. For example, a sensor could include one or more first chambers, one or more second chambers and one or more third chambers. One use for such a configuration would be independent and co-located sensing of distinct chemical species in water (e.g., ammonia and hydrogen sulfide). Sensors as described herein can further be integrated with IoT (Internet of Things) platforms for a more robust solution.

To summarize operation of the ammonia sensor example described below, the sensor includes two membranes: a cation exchange membrane to separate ammonia based on charge, and a gas permeable membrane to separate ammonia based on volatility. Water electrolysis provides electrons at the anode that are matched by transmembrane transport of ammonium and other cations. At the cathode, water electrolysis raises pH, converting ammonium into ammonia, a volatile species that crosses the gas-permeable membrane and is protonated back to ammonium in the acidic trap chamber. The system can be remotely controlled by wireless networks because electricity replaces chemicals as the major input. This technology pivots from electrochemical water treatment to electrochemical water sensing.

The proof-of-concept was established with a centimeter-scale device, in which relative rates of nitrogen reactions and transport are currently being elucidated using varying reactor geometries. It is demonstrated that nitrogen recovery exhibits lower costs, energy input, and emissions than conventional nitrogen management.

The present approach provides deployable water quality sensors that accelerate timely and accurate pollution detection, deployable remediation of chemical spills, and remote monitoring of water treatment systems. Bringing treatment to water rather than conveying water to treatment can potentially address most of the wastewater not collected at treatment plants. In addition, distributed treatment can address the pollution that has already occurred, which must play a pivotal role in treating legacy pollution. To address distributed polluted waters (lake, river, creek, and sea etc.), ammonia-selective treatment technologies are adapted and deployed as ammonia-selective sensors, which is a step toward deployable ammonia sensors for monitoring ammonia in treatment processes. These novel sensors may improve remote ammonia monitoring, in turn accelerating localized understanding of aquatic ammonia dynamics.

Finally, disinfection byproducts that may be discharged from ammonia recovery systems and affect aquatic ecosystems can be measured.

The sensor is expected to play a crucial role in IoT based water quality monitoring for any and every type of water body. With growing concerns of how and when pollutants enter the water body and being able to detect the entry point of such pollutants, the sensor can be effectively and economically be deployed with an IoT platform. The market need for continuous water monitoring is stark as the EPA alone spent 12.5 million dollars (FY 2018) in water quality monitoring, where ammonia monitoring is estimated to be a large portion of that. This issue is even more acute in developing and agricultural-based countries such as India and China where run-off from farms into water bodies is a major concern.

DETAILED DESCRIPTION

1) Introduction

Figure 1A:
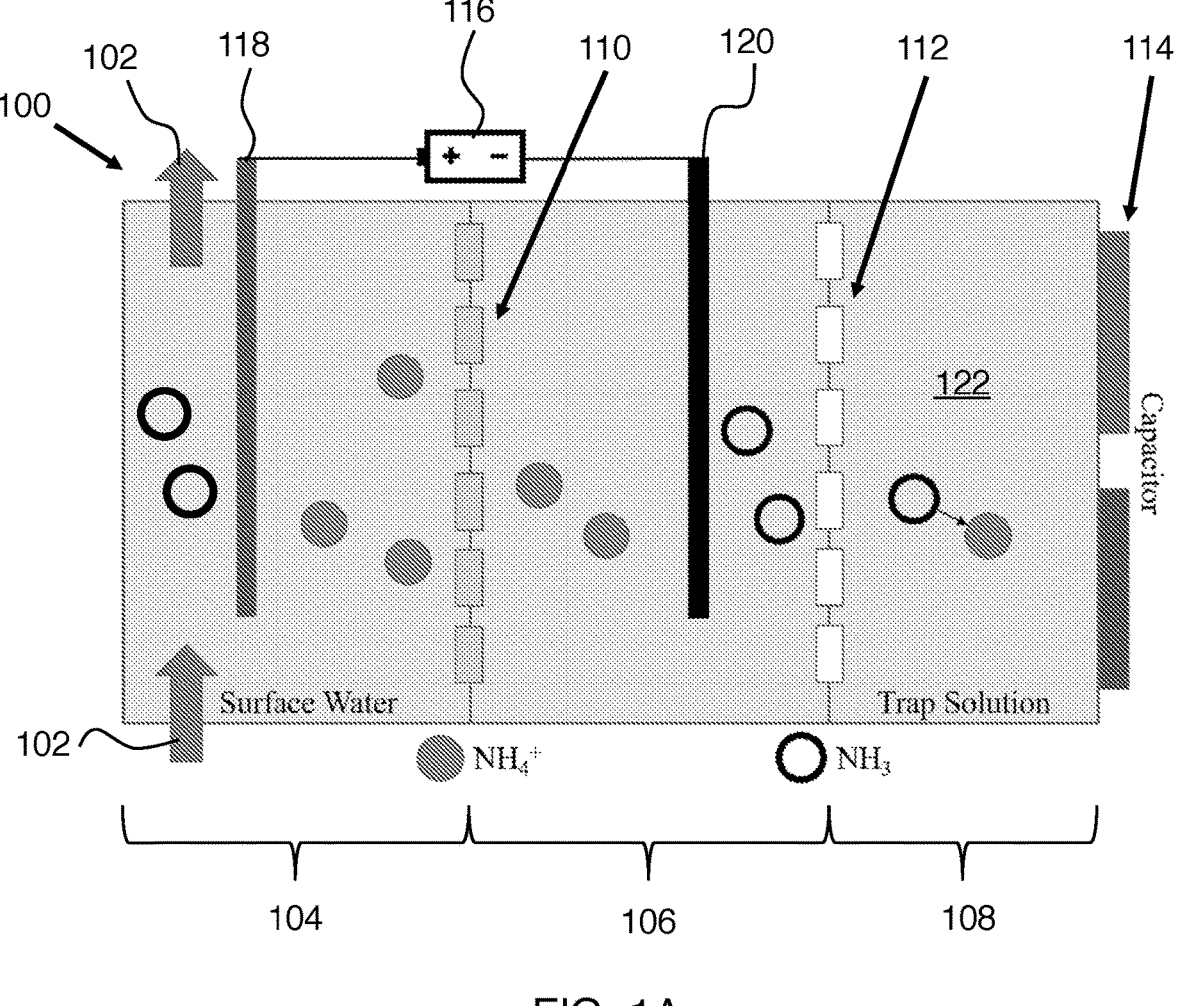
FIGS. 1A-B are two schematic views of an exemplary embodiment of the invention.

Ammonia is one of the most common nutrients discharged in surface waters, and can cause harmful algae blooms that perturb aquatic ecosystems. There is a strong need to monitor pollutants such as ammonia to proactively protect aquatic life by pinpointing areas for remediation before eutrophication. Dissolved ammonia primarily originates from agricultural runoff and sewage treatment effluent. However, existing ammonia sensors limit monitoring frequency due to costly lag times between sampling and measurement. A majority of the measurement tools used to detect dissolved ammonia require extensive personnel involvement (e.g., field test kits), require sample pretreatment to mitigate interference from common water constituents (e.g., $K^+$ for ammonia probes), or require transport to laboratory facilities (such as ion chromatography). Existing methods are also challenged by the spatiotemporal variability exhibited by most surface waters. Based on these shortcomings, there is a demand for real-time and on-site dissolved ammonia sensing to facilitate nutrient control and remediation.

Electrochemical stripping (ECS) can selectively recover total ammonia nitrogen (TAN, $[NH_4^+]+[NH_3]$) from complex matrices, including urine, hydrothermal liquefaction effluent, and anaerobic digester effluent. Specifically, ECS recovers over 93% of ammonia nitrogen as high-purity ammonium sulfate fertilizer with >99% selectivity. Ammonium ions pass through a cation exchange membrane (CEM) via electromigration followed by the formation of ammonia gas in alkaline catholyte. The generated ammonia gas continuously diffuses through a gas permeable membrane (GPM) and dissolves in a trap solution (sulfuric acid). The ECS process causes transient perturbations in conductivity and permittivity of the trap solution, which enables accurate and sensitive ammonium monitoring when paired with capacitive detection.

Capacitive sensing has been significantly developed for applications in detecting a variety of aqueous species. In addition to detecting small perturbations of permittivity it exhibits advantages such as low cost, high sensitivity, and non-invasive observation. In our acrylic sensors, capacitive sensing components do not need to come into direct contact with the solution, because the electromagnetic waves can penetrate plastic materials (insulator) used in sensing chamber designs. Whereas electrochemical sensors often employ conductivity detection to ease integration with existing conductivity sensors, capacitive sensing facilitates highly sensitive measurements. For TAN sensing, low detection limits (<0.5 mg N/L) are useful for anticipating eutrophication.

Here, we report the examined response (e.g., sensitivity) of a three-chamber electrochemical sensor for the detection of TAN in surface waters. In addition, we present our low-cost design approach, which supports immersible operation, as well as wide-spread deployment. To realize our sensor platform, we combined a selective ECS process with a sensitive capacitor to monitor dissolved ammonia. The increase of TAN concentration due to ECS changed the overall permittivity of the trap solution. Then, the permittivity changes were measured with our capacitive sensing at a low power draw (0.11 Joule per measurement). We anticipate the use of the sensor to preemptively monitor eutrophication and aqueous ammonia emissions.

Figure 1B:
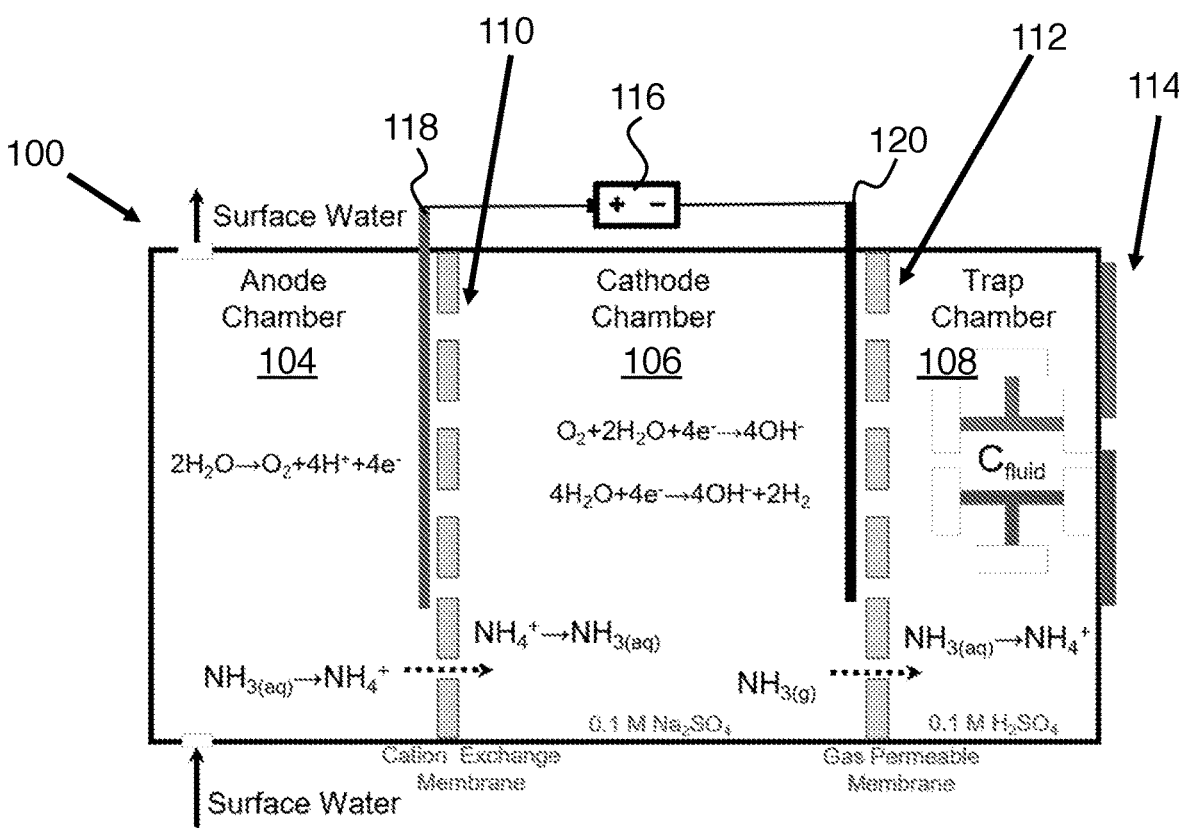
Figure 1C:
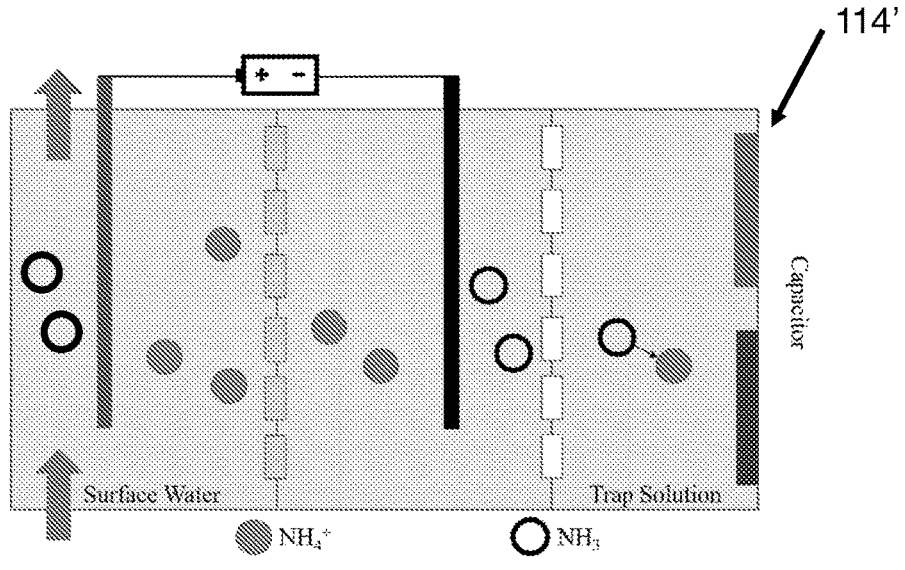
FIG. 1C schematically shows an immersed electrical sensor.

FIG. 1A shows a physical schematic of the three-chamber electrochemical ammonia sensor 100. FIG. 1B is another schematic of sensor 100 with more emphasis on the relevant chemical reactions. Surface water 102 flows through first chamber 104. In practice, surface water 102 could include water from rivers, lakes, and oceans. In this work, a 20 mM ammonium sulfate solution was used as surface water 102 in the experiments and was fed into first chamber 104. Cations migrated to the second chamber 106 through an ion exchange membrane 110, and ammonia gas diffused to the third chamber 108 through a gas permeable membrane 112. In the third chamber ammonium ions were formed by trap solution 122 and measured by an electrical sensor 114. The dotted arrows on FIG. 1B show the direction of nitrogen mass transfer in the three-chamber electrochemical cell. The chemical reactions in the first and second chambers are driven by an electrical source 116 having a first electrode 118 disposed in the first chamber and having a second electrode 120 disposed in the second chamber. FIG. 1C shows a minor variation on this scheme, where electrical sensor 114' is immersed in third chamber 108.

In the following description of this example, it will be convenient to refer to the first, second and third chambers as the anode, cathode and trap chambers, respectively.

2) Materials and Methods

2.1) Electrochemical Sensor Setup

Figure 4:
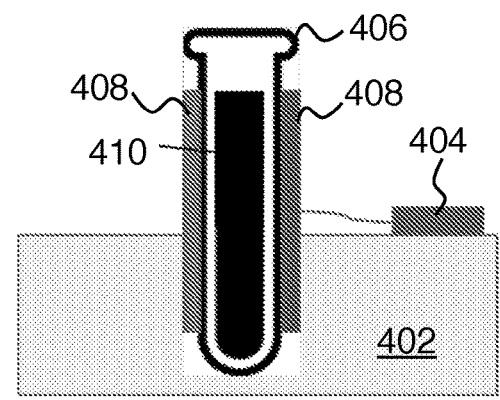
FIG. 4 schematically shows the capacitance measurement setup for this experimental work.
Figure 5:
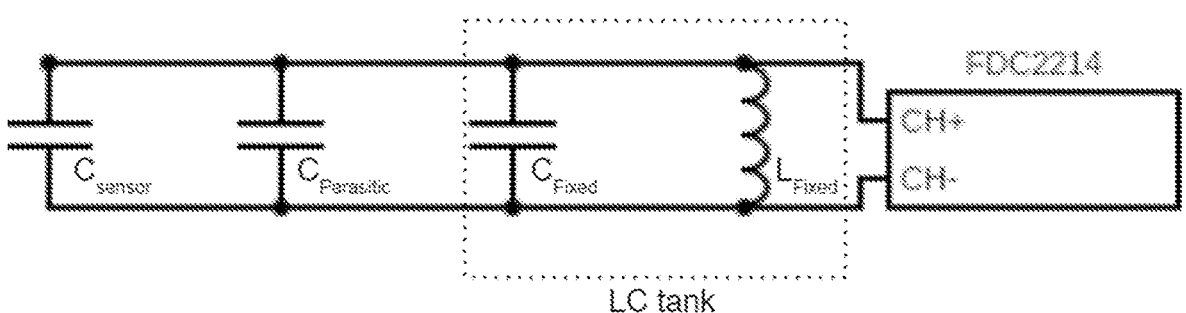
FIG. 5 is a simplified electrical schematic of the inductor-capacitor circuit used with the commercial capacitance-to-digital converter.

We scaled the ECS process down (by a factor of six) from previous studies to achieve a smaller, more deployable sensor. Ammonium formed in the trap chamber was detected using a radiometric capacitive measurement collected from a discrete 28-bit capacitance-to-digital converter with a noise-floor of 0.3 femtofarad (FDC2214, Texas Instruments, Dallas, TX). The capacitive sensing electrodes of capacitive sensor 404 were two copper pads 408 placed on the outside of a 1 mm thick polypropylene test tube 406 containing the solution 410 from the trap chamber (FIG. 4). Here 402 is a Styrofoam box. The electrode configuration can be simplified as a parallel-plate capacitor capable of non-contact capacitive measurements of the sulfuric acid solution. The sensor readout was recorded using a custom-built microcontroller board with an ATSAMD51G19A microprocessor running open-source CircuitPython to configure and read the FDC2214 values, and an ESP32 Wi-Fi co-processor by Espressif Systems for wireless communication (FIG. 5). Post-processing of the capacitive sensor data included removing temperature-dependent artifacts by having a second capacitive sensor placed near the test sensor.

2.2) Sensor Experiments

We used a multichannel potentiostat (Reference 3000, Gamry Instruments, Warminster, PA) to control current and measure potential. Anolyte (20 mM ammonium sulfate), catholyte (0.1 M sodium sulfate), and trap (0.1 M sulfuric acid) solutions were recirculated separately at approximately 8 mL/min through the reactor from 200 mL reservoirs. All solutions were made with nanopure water and reagent-grade chemicals (Thermo Scientific, Waltham, MA). Sodium sulfate was used as catholyte to increase conductivity and overcome internal solution resistance; sulfuric acid was used to trap ammonia gas, forming ammonium ions. We measured the samples from the trap chamber using our capacitive sensor that measured minute changes in solution permittivity (FIGS. 1A-B).

2.3) Analytical Methods

Aqueous ions were detected and quantified by Dionex ICS-6000 (Thermo Scientific, Waltham, MA) ion chromatography (IC). A Dionex IonPac CS12A Analytical Column was used for ammonium detection with a resolution of 0.01 mg N/L of ammonium (30° C.; 20 mM methanesulfonic acid eluent at 1 mL/min). Conductivity was measured with a pH/conductivity meter (SevenCompact Cond S213, Mettler Toledo, Columbus, OH) with 0.001 μS/cm resolution.

3) Results and Discussion

3.1) Examine Capacitive Sensing Response

Figure 2A:
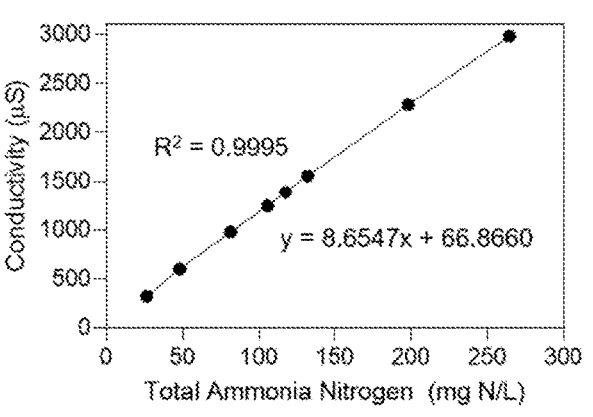
FIG. 2A shows the relation between Total Ammonia Nitrogen (TAN) and conductivity in a control experiment (without electrochemical ammonia concentration).
Figure 2B:
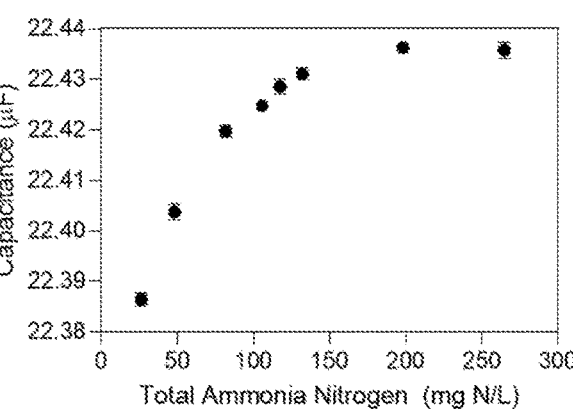
FIG. 2B shows the relation between Total Ammonia Nitrogen and capacitance in the control experiment.

FIGS. 2A-B show results of the conductivity and capacitance response to ammonium sulfate solution. FIG. 2A shows the relationship between conductivity and total ammonia nitrogen. FIG. 2B shows the relationship between capacitance and total ammonia nitrogen. Error bars represent ±three standard deviations and are not shown if smaller than the symbol.

Figure 6:
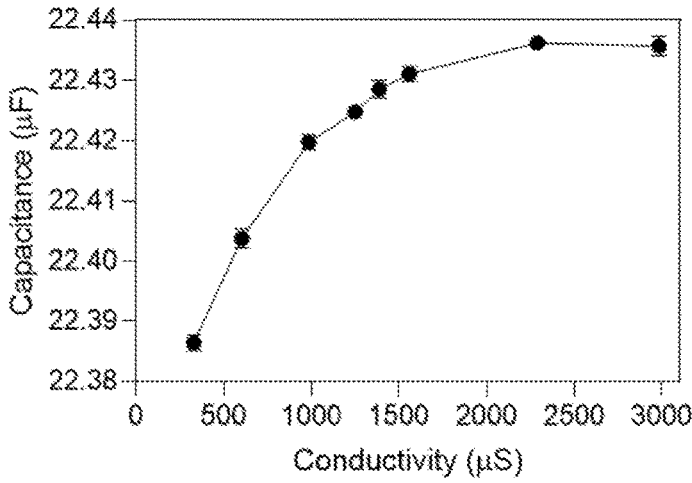
FIG. 6 shows the relationship of capacitance with conductivity in ammonium sulfate.

Conductivity and capacitance measurements provide fast and simple approaches to examine the capacitive sensing characteristics. Conductivity can also act as a more established benchmark for our capacitance measurements. First, we measured the conductivity and capacitance in different concentrations of ammonium sulfate solutions to validate our capacitor. As expected, TAN concentration increased linearly with conductivity (FIG. 2A), based on previous reports that conductivity increases with salt concentration. The capacitance also increased with the TAN concentration and eventually plateaued (FIG. 2B). This response is in agreement with previous reports that capacitance increases with salt concentration. As expected for an external capacitor (where the capacitor does not come into direct contact with the solution), capacitance values asymptotically plateaued at the walls between the capacitor and solution. Thus, capacitance varied directly with conductivity for the simplest setup of detection in ammonium sulfate solution (FIG. 6).

3.2) Testing in the Three-Chamber Cell

Figure 3A:
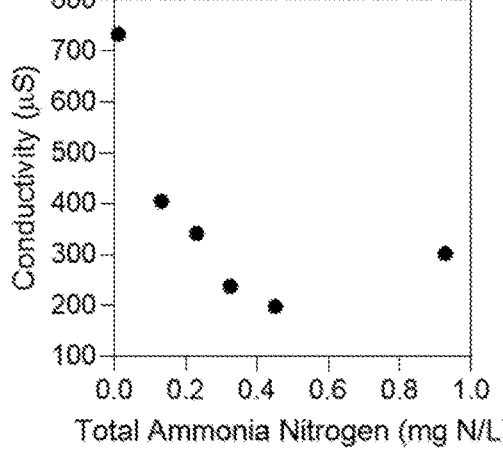
FIG. 3A shows the relation between Total Ammonia Nitrogen and conductivity with electrochemical ammonia concentration.
Figure 3B:
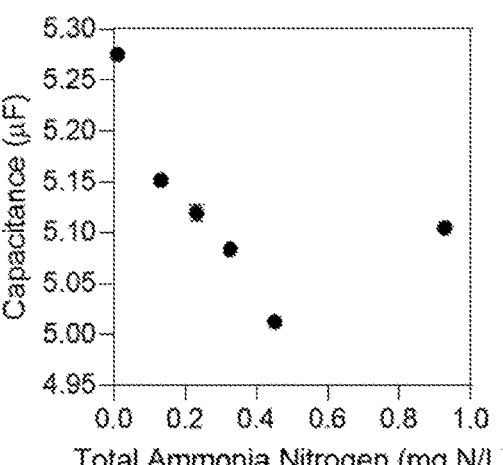
FIG. 3B shows the relation between Total Ammonia Nitrogen and capacitance with electrochemical ammonia concentration.

FIGS. 3A-B show results of conductivity and capacitance tested in the trap chamber. FIG. 3A shows the relationship between the conductivity and total ammonia nitrogen. FIG. 3B shows the relationship between the capacitance and total ammonia nitrogen. Error bars represent ±three standard deviations and are not shown if smaller than the symbol.

We tested our three-chamber cell (combining the ECS process and capacitive sensing) with 20 mM ammonium sulfate as the anodic feed. These experiments reflect remote sensing with higher fidelity, especially by including the conversion of ammonium to volatile ammonia in the cathode and back to aqueous $NH_4^+$ in the trap (Equation 1).

$$NH_3+H^+\leftrightarrow NH_4^+ \tag{1}$$

Major determinants of conductivity were the mobility of the ions (K in equation 2) and the ion's collision cross-sectional area (Ω). Ammonium has a larger collision cross-sectional area than protons, which it replaces in the trap chamber during electrochemical stripping. The large collision cross-section results in lower mobility of the ions, and thus a drop in conductivity. Therefore, the conductivity decreases linearly in the range of 0-0.4 mg N/L as TAN concentration increases (FIG. 3A).

$$K = \sqrt{\frac{2\pi}{\mu kT}} \frac{3q}{16N} \frac{1}{\Omega} \tag{2}$$

Equation 2 shows the relationship between ion mobility and cross-sectional area, where q is the charge of the ion, N is the number density of the ion, k is the Boltzmann constant, T is the absolute temperature, and μ is the reduced mass of the ion-neutral pair. During electrochemical stripping, all parameters stayed constant except for TAN concentration and collision cross-sectional area.

The capacitance (C in equation 3) also decreased linearly as the TAN concentration increased in the range of 0-0.4 mg N/L (FIG. 3B). For a parallel plate capacitor, we have $$C = \frac{\epsilon_o \epsilon_r A}{d} \tag{3}$$

where A is the area of the parallel plate capacitor, d is the separation of the parallel plate capacitor, $\epsilon_0$ is the free space permittivity, and $\epsilon_r$ is the relative permittivity.

In an exemplary model, capacitance is related to under-lying physical parameters as follows. First we determine $\epsilon_\infty$ according to $$\frac{\epsilon_\infty - 1}{\epsilon_\infty + 2} = \frac{1}{3\epsilon_0} \frac{N_A}{v} \sum_i x_i \alpha_{0,i} \tag{4}$$

where $N_A$ is Avogadro's constant, $v$ is the molar volume, $x_i$ is the mole fraction of component i and $\alpha_{0,i}$ is the molecular polarizability of component i.

Next we calculate Kirkwood g-factors $g_i$ that account for local dipolar correlations due to fluid structure according to $$g_i = 1 + \sum_j \frac{z_{ij} P_{ij} \cos \gamma_{ij}}{P_i \cos \theta_{ij} + 1} \frac{\mu_{0,j}}{\mu_{0,i}} \tag{5}$$

where $z_{ij}$ is the coordination number of molecule j around a central molecule i, $P_{ij}$ is the probability that molecule i is is associated with molecule j, $\mu_{0,i}$ is the vacuum dipole moment of molecule i, $P_i$ is the probability that molecule i is associated with any of its S nearest neighbors (i.e., $P_i = \Sum_{j \in s} P_{ij}$), $\theta_{ij}$ is the hydrogen bond angle bond between molecule j in shell around molecule i and the second shell neighbor, and $\gamma_{ij}$ is the angle between the dipole moment of central molecule i and surrounding molecule j.

Next we account for unbound components by defining $\Theta_i$ to be the fraction of component i that is not bound to an ion $$\Theta_i = 1 - \Sum_j^{ions} P_{ij}. \tag{6}$$

Finally, the relative permittivity $\epsilon_r$ is given by $$\frac{(2\epsilon_r + \epsilon_\infty)(\epsilon_r - \epsilon_\infty)}{\epsilon_r} = \left(\frac{\epsilon_\infty + 2}{3}\right)^2 \frac{N_A}{\epsilon_0 k_B T v} \sum_i x_i \Theta_i g_i \mu_{i,0}^2. \tag{7}$$

A change in $\epsilon_r$ leads to a change in capacitance according to the capacitor geometry, as is well known in the art. For example, equation 3 relates capacitance to $\epsilon_r$ for a parallel-plate geometry.

When TAN concentration increased in the trap chamber, protons combined with ammonia gas to form ammonium ions, and the number density and molecular polarizability were decreased. Therefore, according to equations 4-7, the capacitance changes proportionally to the addition of ions in sulfuric acid. The correlation of our sensor under 0.4 ppm showed a linear relationship (FIGS. 7A-B) and the capacitance showed a similar increase as conductivity in the trap chamber (FIG. 7C).

Conductivity and capacitance exhibited a linear relationship between 0 and 0.4 mg N/L of TAN (FIGS. 3A-B). Further investigation is required to explain the increasing trend in conductivity and capacitance above 0.4 mg N/L of TAN. A possible explanation for the rise in conductivity and capacitance after 0.4 mg N/L could be the overall increase in the number density (n) and the molecular polarizability ($\alpha$). The synergistic effect of n and a may lead to an increase in conductivity and capacitance after 0.4 mg N/L. The resolution of our sensor allows linear detection in the range of 0.01 to 0.4 mg N/L, which would facilitate the distinction of water quality leading up to observable eutrophication. More specifically, this detection range could distinguish between putative "good," "fair", and "poor" dissolved inorganic nitrogen indicators for coastal Gulf of Mexico environments, which is below 0.4 mg N/L. The detection range of our sensor was confirmed by the calibration curve of ion chromatography at low ammonium concentrations (under 0.4 mg N/L, FIG. 8). Because ECS has already been demonstrated to be selective in various real wastewaters that are more challenging than typical surface waters, we focused on combining ECS with capacitive sensing and expect similar selectivity in surface water.

3.3) Sensor Comparison

After validating selective and linear ammonia detection with our sensor design, we compared our ammonium sensor with other sensors reported from literature to gain a sense of our platform's feasibility in real-world applications. The primary factors of interest are cost, sensitivity, selectivity, and deployability. Compared to other commercial and reported ammonia sensors, our integrated capacitive sensing and ECS sensor is compact, economical, and adequately sensitive; therefore, it is suitable for remote and continuous deployment. Sensor costs were determined based on either quotation found on the manufacturer's website or the cost of the most expensive component used in the setup. Often, costs are not reported in literature and have been extrapolated based on similar measurements available in industry. The total cost of our ECS and capacitive sensing unit is $29 based on the materials we used for our lab setup. Once integrated, the overall size of the system can be under 5×5×5 $cm^3$ and has energy consumption lower than 0.11 Joule for each reading. This low power draw facilitates remote and continuous deployment, because a single battery can support hourly measurements of our sensor for over 3 years. The sensitivity-cost ratio is useful for environmental applications where a large number of sensors are required and the budget for these sensors is limited. The deployed sensors must be sufficiently sensitive but also low in cost to enable mass deployment. Our sensor exhibited a low cost and moderate sensitivity compared with literature and commercial sensors, and a very competitive value calculated by sensitivity-cost ratio.

4) Conclusion

By combining electrochemical stripping and capacitive sensing, we designed a highly selective and sensitive sensor for dissolved ammonia measurements in surface water. The low cost of our sensor (total $29) along with the low energy draw per reading (0.11 Joule) makes our sensor well-suited for remote deployment with IoT nodes. With over 99% selectivity of dissolved ammonia and a 0.3 femtofarad noise floor, our sensor is competitive with others reported in literature and commercially. Future work includes deploying sensors for real-time testing in surface waters and investigating the critical point for capacitance and conductivity at 0.4 mg N/L. Our ammonia sensor facilitates cost-effective and accurate daily readings in surface water. The data collected from the sensors can be a tool to proactively monitor our surface water, protect the surface water from harmful algae blooms, and pinpoint sources of pollution in real-time. The development of low-cost deployable sensors will improve the understanding of surface water ammonia dynamics and interventions to manage nutrients in aquatic ecosystems.

5) Supplemental Information

FIG. 4 is a schematic of the external capacitive sensor setup. The copper pads 408 placed on the 1 mm thick polypropylene test-tube 406 with 1 cm in width and 4 cm in length, and were placed on the outside of the test-tube facing opposite of each other. The second capacitive sensor utilized a second channel of the FDC2214 converter and contained no electrodes beyond the fixed capacitor of the inductor-capacitor circuit. Care was taken to limit time-dependent stray capacitances by isolating the electrode setup using several centimeters of a low-dielectric material (polystyrene foam 402).

Experiments were performed in a three-chamber parallel plate reactor in which three square acrylic frames (internal dimensions: 2×6.5×1 cm³) were bolted together between two larger square Perspex plates (5.5×10×0.5 cm³) to create the anode, cathode, and trap chambers. The anode and cathode chambers were separated by a CEM (CMI-7000, base materials: gel polystyrene crosslinked with divinylbenzene, functional group: sulfonic acid, pore size<5 nm, Membranes International Inc, Ringwood, NJ). The cathode and trap chambers were separated by a polypropylene GPM (CLARCOR QL 822, pore size<0.3 μm, CLARCOR Industrial Air, Overland Park, KS). Membranes were hydrated and expanded by immersion in nanopure water (resistivity: 18.2 MΩ·cm) for 12 hours before use. In all experiments, stainless steel (316 stainless steel, Small Parts, Plymouth, MI) was used as the cathode and carbon fiber cloth (ACER Racing, Santa Monica, CA) was used as a low-cost anode. The primary electrode reactions are anodic oxygen evolution reaction (OER), cathodic oxygen reduction reaction (ORR), and cathodic hydrogen evolution reaction (HER). Ammonium ions were converted to ammonia gas by combining with hydroxide ions in the cathode chamber, and the ammonia gas was trapped by sulfuric acid in the trap chamber.

FIG. 5 is a simplified electrical schematic of the inductor-capacitor circuit used with the commercial capacitance-to-digital converter.

The FDC2214 capacitance-to-digital integrated circuit is capable of absolute capacitance measurements by quantifying frequency shifts of an inductor-capacitor (LC) resonator, also known as an "LC tank". An 18 μH inductor and 33 pF capacitor with 0±30 ppm/° C. temperature variation were used to create an LC tank with a resonant frequency of 6.5 MHz as described by equation 8:

$$f = \frac{1}{2\pi\sqrt{LC}} \tag{8}$$

where L is the inductance, and C is the capacitance. Using equation 8, the capacitance of the sensor electrodes can be described as a sum of the parallel capacitances:

$$C_{sensor} = \frac{1}{L(2\pi f_{sensor})^2} - (C_{LC} + C_{parasitic}) \tag{9}$$

where $f_{sensor}$ is the frequency measured by the FDC2214, and $C_{LC}$ and $C_{parasitic}$ are the capacitances of the LC tank and stray parasitic capacitances, respectively. Shifts in the sensor frequency are measured comparatively by feeding a known frequency of 40 MHz into the FDC2214 from an external temperature compensated crystal oscillator (TCXO). The LC tank with sensor electrodes attached was driven at 0.747 mA with a deglitch value of 10 MHz.

FIG. 6 shows the relationship of capacitance with conductivity in ammonium sulfate. Error bars represent±three standard deviations, and are not shown if smaller than the symbol.

Figure 7A:
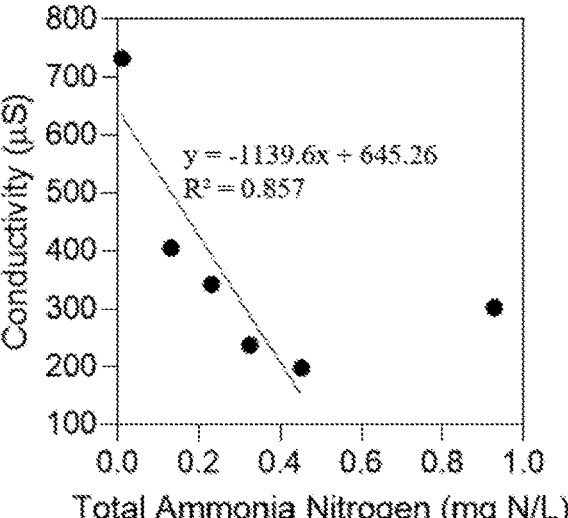
FIG. 7A shows the correlation of conductivity with TAN in the three-chamber electrochemical cell.
Figure 7B:
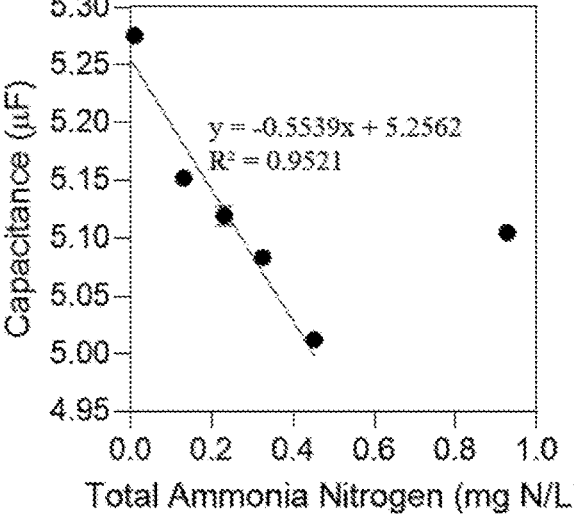
FIG. 7B shows the correlation of capacitance with TAN in the three-chamber electrochemical cell.
Figure 7C:
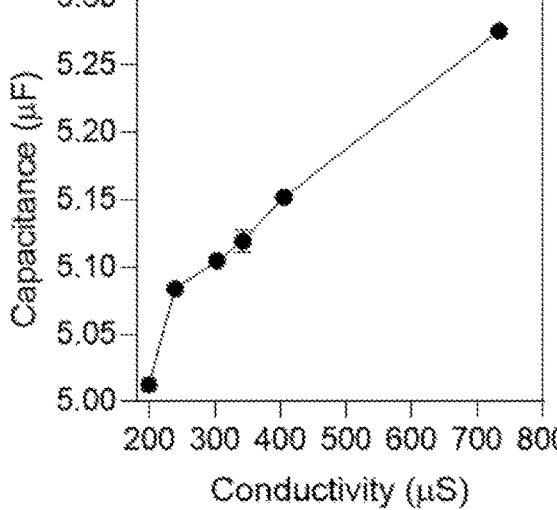
FIG. 7C shows the relationship of capacitance with conductivity in the three-chamber electrochemical cell.

FIG. 7A shows the correlation of conductivity with TAN and FIG. 7B shows the correlation of capacitance with TAN. FIG. 7C shows the relationship of capacitance with conductivity in the three-chamber electrochemical cell. Error bars represent ±three standard deviations, and are not shown if smaller than the symbol.

Figure 8:
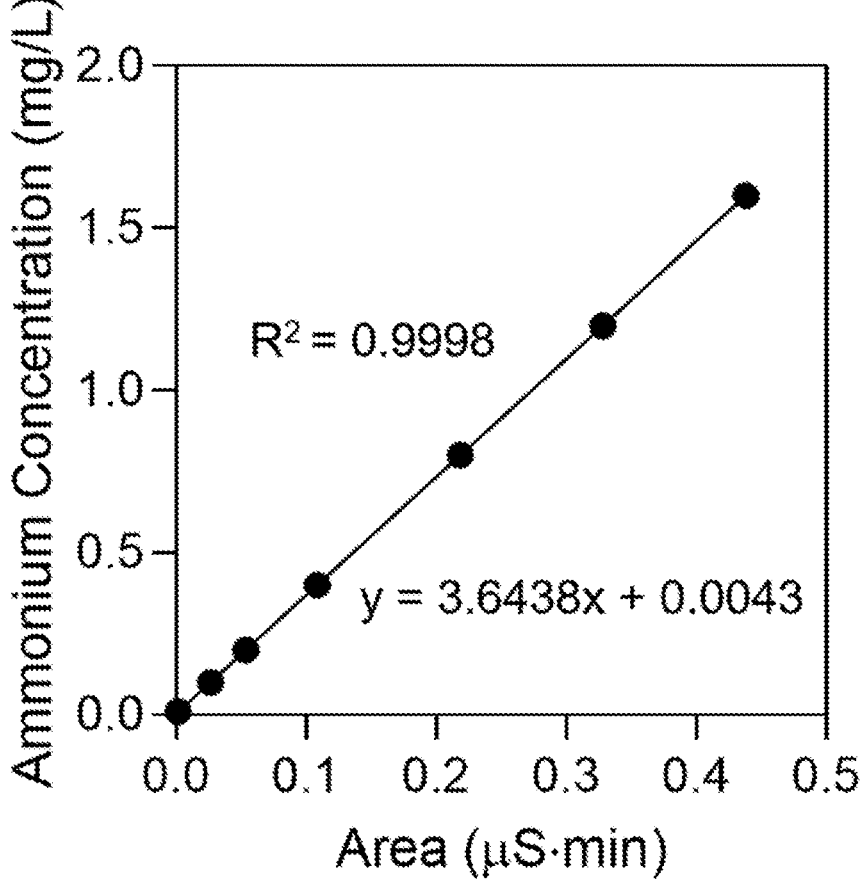
FIG. 8 is a calibration curve of ion chromatography at low ammonium concentration.

FIG. 8 is a calibration curve of ion chromatography at low ammonium concentration. The cation standard includes 50 mg $Li^+$/L, 200 mg $Na^+$/L, 400 mg $NH_4^+$/L, 200 mg $K^+$/L, 200 mg $Mg^{2+}$/L, and 1000 mg $Ca^{2+}$/L. The cation standard was diluted 4,000 times, 2,000 times, 1,000 times, 500 times, 375 times, and 250 times from the parent standard.

The invention claimed is:

1. A deployable sensor for detection of a gaseous analyte in water, the deployable sensor comprising:
   a first chamber, a second chamber and a third chamber;
   an ion exchange membrane configured such that ions would pass through the ion exchange membrane between the first chamber and the second chamber;
   a gas permeable membrane configured such that dissolved gas can pass through the gas permeable membrane between the second chamber and the third chamber;
   an electrical source configured to provide a voltage between a first electrode in the first chamber and a second electrode in the second chamber such that
   i) an analyte-ion corresponding to the gaseous analyte is generated in the first chamber, and
   ii) the gaseous analyte is generated in the second chamber from analyte-ions that have passed through the ion exchange membrane;
   wherein the third chamber includes a solution configured to generate the analyte-ion from gaseous analyte that has passed through the gas permeable membrane;
   an electrical sensor configured to detect a third concentration of the analyte-ion in the third chamber;
   wherein the electrical sensor is configured to have an electrical property that is responsive to the third concentration of the analyte-ion in the third chamber.

2. The deployable sensor of claim 1, wherein a concentration of the analyte in the first chamber is determined from the third concentration of the analyte-ion in the third chamber by assuming a capture rate of 90% or more of the analyte in the first chamber.

3. The deployable sensor of claim 2, wherein a linear relationship is established between a first concentration of the analyte-ion in the first chamber and the third concentration of the analyte-ion in the third chamber based on one or more operating parameters of the sensor.

4. The deployable sensor of claim 3, wherein the one or more operating parameters of the sensor are selected from the group consisting of: applied bias, fluid flow rates, and sensing time.

5. The deployable sensor of claim 1, wherein the gaseous analyte is selected from the group consisting of ammonia, hydrogen sulfide and carbon dioxide.

6. The deployable sensor of claim 1, wherein the ion exchange membrane is an anion exchange membrane.

7. The deployable sensor of claim 1, wherein the ion exchange membrane is a cation exchange membrane.

8. The deployable sensor of claim 1, wherein the electrical sensor is a capacitive sensor.

9. The deployable sensor of claim 1, wherein the electrical sensor is a conductivity sensor.

10. The deployable sensor of claim 1, wherein the electrical sensor is immersed in the third chamber.

11. The deployable sensor of claim 1, wherein the electrical sensor is not immersed in the third chamber.

\* \* \* \* \*